(12) United States Patent
Eng

(10) Patent No.: US 7,534,202 B2
(45) Date of Patent: May 19, 2009

(54) SYSTEM AND METHOD FOR HIGH DOSE RATE RADIATION INTRACAVITARY BRACHYTHERAPY

(75) Inventor: Tony Y. Eng, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/243,474

(22) Filed: Oct. 4, 2005

(65) Prior Publication Data

US 2006/0116546 A1    Jun. 1, 2006

Related U.S. Application Data

(60) Provisional application No. 60/615,659, filed on Oct. 4, 2004, provisional application No. 60/629,282, filed on Nov. 18, 2004.

(51) Int. Cl.
 *A61N 5/00* (2006.01)
(52) U.S. Cl. .......................................................... 600/3
(58) Field of Classification Search ............... 600/1, 600/2, 3, 6, 7; 604/523, 915–921; 606/192–193, 606/198; 128/830–831, 833, 836, 839
See application file for complete search history.

(56) References Cited

U.S. PATENT DOCUMENTS

| | | | |
|---|---|---|---|
| 4,430,076 A | 2/1984 | Harris | |
| 5,277,201 A | 1/1994 | Stern | |
| 5,429,582 A | 7/1995 | Williams | |
| 5,443,470 A | 8/1995 | Stern et al. | |
| 5,713,942 A | 2/1998 | Stern et al. | |
| 5,797,948 A * | 8/1998 | Dunham | 606/194 |
| 5,913,813 A | 6/1999 | Williams et al. | |
| 5,931,774 A | 8/1999 | Williams et al. | |
| 5,935,098 A | 8/1999 | Blaisdell et al. | |
| 6,041,260 A | 3/2000 | Stern et al. | |
| 6,083,148 A | 7/2000 | Williams | |
| 6,254,601 B1 | 7/2001 | Burbank | |
| 6,390,968 B1 | 5/2002 | Harmon | |
| 6,413,204 B1 | 7/2002 | Winkler et al. | |
| 6,540,655 B1 * | 4/2003 | Chin et al. | 600/3 |
| 6,602,251 B2 | 8/2003 | Burbank et al. | |
| 6,607,477 B1 * | 8/2003 | Longton et al. | 600/3 |
| 6,685,618 B2 | 2/2004 | Tam et al. | |
| 6,699,171 B2 | 3/2004 | Harmon | |
| 6,764,488 B1 | 7/2004 | Burbank et al. | |
| 7,163,504 B1 * | 1/2007 | Chiu et al. | 600/3 |
| 2001/0014805 A1 | 8/2001 | Burbank et al. | |
| 2003/0114878 A1 * | 6/2003 | Diederich et al. | 606/192 |
| 2003/0149330 A1 * | 8/2003 | Geitz | 600/3 |
| 2003/0153803 A1 | 8/2003 | Harmon | |

(Continued)

*Primary Examiner*—Charles A Marmor, II
*Assistant Examiner*—Christine D Hopkins
(74) *Attorney, Agent, or Firm*—Meyertons, Hood, Kivlin, Kowert & Goetzel, P.C.; Eric B. Meyertons

(57) ABSTRACT

The apparatus, method and system for performing a high dose rate brachytherapy procedure in a body cavity may include an at least partially indwelling multi-lumen catheter with a plurality of inflatable balloons coupled thereto. A lumen may be adapted to receive radiation seeds. The balloons, when inflated, may be adapted to administer a substantially uniform radiation isodose to the body cavity. Some embodiments may be well suited to performing intrauterine brachytherapy for the treatment of endometrial carcinoma.

28 Claims, 3 Drawing Sheets

U.S. PATENT DOCUMENTS

2003/0166990 A1 9/2003 Trauthen et al.
2003/0216759 A1 11/2003 Burbank et al.
2005/0240074 A1 10/2005 Lubock

* cited by examiner

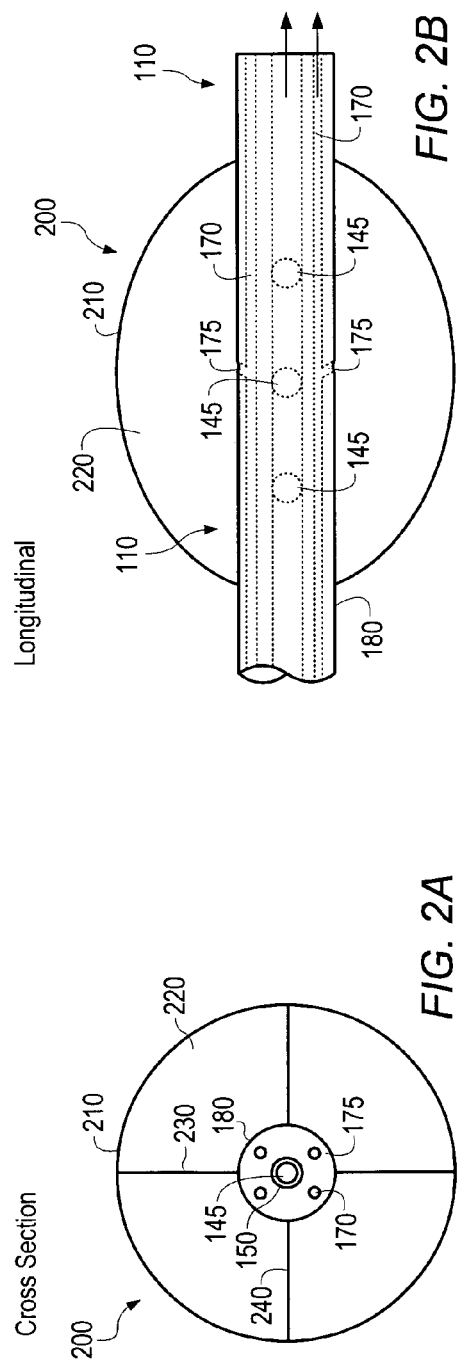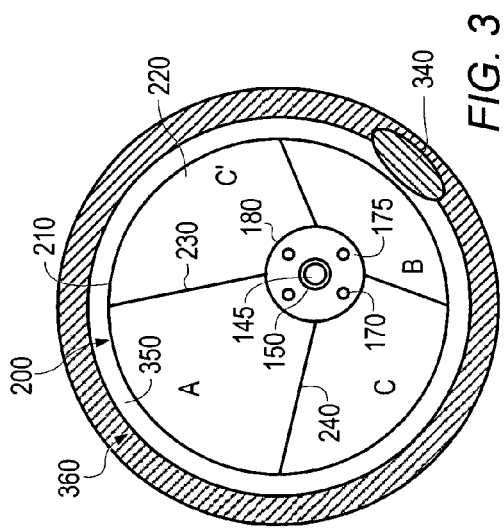

SYSTEM AND METHOD FOR HIGH DOSE RATE RADIATION INTRACAVITARY BRACHYTHERAPY

CROSS-REFERENCE TO RELATED APPLICATIONS

This application claims the benefit of priority under 35 U.S.C. 119 (d)(e) to Provisional Patent Application Ser. No. 60/615,659, entitled "SYSTEM AND METHOD FOR HIGH DOSE RATE RADIATION BRACHYTHERAPY FOR ENDOMETRIAL CARCINOMA" filed Oct. 4, 2004 and to Provisional Patent Application Ser. No. 60/629,282, entitled "SYSTEM AND METHOD FOR HIGH DOSE RATE RADIATION INTRACAVITARY BRACHYTHERAPY," filed Nov. 18, 2004. The above-cited applications are commonly assigned with the present invention, and the entire contents thereof are incorporated by reference as though fully set forth herein.

BACKGROUND

1. Field of Invention

The present invention generally relates to systems and methods for administering intracavitary brachytherapy to subject.

2. Description of Related Art

Endometrial carcinoma, a malignant adenocarcinoma of the glandular epithelium lining the inner wall of the uterus, is one of the most common and serious disorders affecting the endometrium of post-menopausal women. Endometrial carcinomas represent an increasingly frequent tumor occurrence in industrialized countries. For example, in 1997, an estimated 170,000 new cases of endometrial carcinoma were diagnosed worldwide. The high occurrence of this malignancy necessitates the development of new therapeutic treatment alternatives. Moreover, early eradication of the carcinoma generally results in a more favorable prognosis for the patient. While surgical removal of the tumor is a preferred method of treatment, there may be some situations when a patient is unable to tolerate surgery. In some situations, a physician may prescribe one or more courses of preoperative radiation therapy. In yet further situations, surgery may be contraindicated or, particularly in the case of early stage carcinoma, even unnecessary. Additionally, it may be advisable for a patient who has undergone surgery to remove the tumor to undergo one or more courses of radiation therapy to eradicate any remaining tumor cells that may not have been excised.

Radiation therapy is used extensively to treat endometrial malignancies, either pre-operatively, as adjuvant therapy after surgery for patients with greater than stage IA disease, as primary therapy for patients unable to tolerate surgery, or to treat recurrences following surgery. Radiation therapy has been used for uterine cancers for over a century, and may be administered as either external beam treatment, brachytherapy, or both. In some cases, curative intracavitary brachytherapy may represent the most desirable treatment option. Curative intracavitary brachytherapy is frequently used to treat malignancies of the vagina, cervix, and endometrium (the lining of the uterus). Treatment of the endometrium by intracavitary brachytherapy may be referred to herein as intrauterine brachytherapy. While early stage tumors are more responsive to intracavitary implants, more extensive tumors may require treatment with interstitial implants and may involve a combination of external beam radiation therapy and intracavitary and/or interstitial brachytherapy.

Brachytherapy may also be described according to the length of time that a procedure is performed. Low dose rate (LDR) treatments typically require several days if the radioactive sources are temporarily placed in tissue. In some cases, permanent or semi-permanent implants may be preferred, wherein the materials remain in the tissue for a substantial portion of time. During most LDR brachytherapy procedures, a dose of radiation in the range of about 0.4-0.8 Gy/hr is administered. High dose rate (HDR) brachytherapy typically uses high specific activity gamma-emitting radionuclides to deliver a much greater dose (usually >0.4 Gy/min) of radiation to the site than what is administered using LDR brachytherapy. As such, HDR brachytherapy procedures are shorter in duration, and usually last less than an hour. HDR brachytherapy allows precise delivery of the radiation dose prescribed by the physician. The short treatment times, the amenability to performing HDR procedure on outpatient basis, and accurate radiation delivery and improved patient comfort and compliance are all advantages of HDR brachytherapy.

Methods of brachytherapy may be broadly described as manual, in which the radioactive material is placed at the body by hand, or remote, in which placement of the radioactive material may be at least partially or entirely automated. An automated device that may be used to place a radioactive material during a brachytherapy procedure is typically referred to in the art as "a remote afterloader". A representative, though non-limiting, example of a remote afterloader is the VariSource® remote afterloader manufactured by Mick Radio-Nuclear Instruments, Inc.

The basic approaches that are used to deliver intracavitary brachytherapy for gynecologic cancer include, but are not limited to, disposable afterloading Heyman capsules or tandems with colpostats.

Heyman capsules are described in "An aid to computerization of Heyman afterloading system." by Boles and Cook, which is fully incorporated herein by reference, and are available commercially. Heyman Capsules are especially suited to a large uterus, and the current practice is to load as many capsules into the uterus as possible, to stretch the uterus and obtain the best isodose profile. Heyman capsules are available in diameters of 6, 8 and 10 mm and lengths of 2-3 cm. Heyman capsules may be introduced into the uterus, through the dilated cervix, using inactive metallic guides. Typically, at least four Heyman capsules are inserted during a procedure, and often a physician may decide that as many as ten may be necessary. A problem encountered with Heyman capsules is that they have relatively thick stems. This may require continued dilation of the cervical canal (such as, for example, with Hegar dilators) after a few capsules have been inserted, resulting in added discomfort to the patient. Furthermore, since Heyman capsules are numbered, they should always be removed in the reverse order in which they were inserted to avoid jamming.

For patients with small uteri, it may be preferable to administer intrauterine brachytherapy with one or more tandems (in lieu of Heyman capsules) with attached colpostats (which may also be referred to as "ovoids"). Similar techniques used to administer brachytherapy for cervical cancer, such as the Henshke or Fletcher-Suit systems, may be used for intrauterine brachytherapy applications. Tandems are placed in the uterus using a device known as a "tandem and ovoid" applicator. A tandem and ovoid applicator includes a hollow metal tube (the tandem) that is inserted through the cervix into the endometrial cavity. The tandem is about 10 inches long and about as thin as a pencil. The ovoids are hollow metal capsules that are small enough to fit in the vagina and through the dilated cervix. The tandem and ovoid applicator are usually surgically inserted, under anesthesia, in a procedure that may take as long as thirty minutes. As such, intrauterine brachytherapy procedures using tandem and ovoids techniques may require the patient to remain hospitalized, sometimes as long as two days. Radiation therapy is given through the tandem and ovoid applicator by placing radioactive capsules or seeds inside the hollow portions of the applicator.

The American Brachytherapy Society recommends that the treatment plan for high-dose-rate brachytherapy for endometrial carcinoma should be optimized to conform to the target volume as much as possible, and that applicator selection should be based on patient and target volume geometry. Ideally, an appropriate applicator that will administer a substantially homogeneous dose of radiation (i.e. an isodose) to the entire uterus should be selected. These recommendations are set forth in Nag et al., "The American Brachytherapy Society recommendations for high-dose-rate brachytherapy for carcinoma of the endometrium." *International Journal of Radiation Oncology Biology Physics*, 2000, Volume 48, pages 779-790, which is incorporated by reference as though fully set forth herein.

While the brachytherapy systems and methods described above are widely used, they typically, due in part to anatomical variations in the shape, thickness, orientation and size of the uterus of individual patients, do not deliver a substantially uniform isodose to the entire uterus. Moreover, because of the somewhat invasive nature of the above mentioned systems, and because patients may typically require multiple treatments, a system that shortens the procedure time and eases the discomfort experienced by the patient, and is thus more readily tolerated, would be advantageous.

Interstitial brachytherapy systems have been used to administer postoperative LDR or HDR brachytherapy to the tissue surrounding a resection cavity. U.S. Pat. No. 5,913,813 entitled "Double-wall balloon catheter for treatment of proliferative tissue" and U.S. Pat. No. 6,413,204 entitled "Interstitial brachytherapy apparatus and method for treatment of proliferative tissue diseases" describe an interstitial brachytherapy apparatus for delivering radioactive emissions to a surgical resection cavity including a central bitumen catheter with an inflatable balloon coupled to the distal end of the apparatus. U.S. Pat. No. 5,931,774 entitled "Inflatable devices for tumor treatment" describes an implantable LDR brachytherapy catheter with distal inflatable balloon that is inflated with a radioactive treatment fluid. While these systems work well for interstitial brachytherapy applications, their use in intrauterine applications may be limited due to variations in the shape, thickness, orientation and size of the uterus of individual patients.

There is still a need for a brachytherapy system that may be used to deliver a radioactive source residing in a flexible catheter that may easily be introduced into the uterus, where the apparatus maintains the catheter and the radioactive source in a position that delivers a substantially uniform radiation isodose with a desired intensity to the entire uterus.

SUMMARY

In an embodiment, an apparatus for performing brachytherapy in a body cavity may include an elongated catheter with a plurality of lumens that substantially extend along the length of the catheter. The catheter may be at least partially composed of a flexible material. The catheter may include a proximal end and a distal end. The distal end of the catheter may be adapted to be inserted into a body cavity of a patient undergoing radiation therapy. At least some of the lumens may, in some embodiments, be continuous with each other. In other embodiments, the lumens may be discontinuous with each other. One or more of the lumens may be continuous with the surface of the proximal end of the catheter. One or more of the lumens may be continuous with the surface of the distal end of the catheter. One or more of lumens may further be adapted to receive one or more radiation seeds. A radiation seed may administer a prescribed dose of radiation to the surrounding tissue. In an embodiment, a radiation seed may reside in a lumen at the distal end of the catheter. In an embodiment, a radiation seed may be placed at the distal end of a catheter lumen by a radiation seed-loading device. In an embodiment, a radiation seed may be placed in a catheter lumen at or near the time of manufacture of the catheter. A pharmacological composition may be administered through one or more of the lumens of the catheter.

In an embodiment, the distal end of a catheter may be coupled to one or more inflatable balloons. The balloons coupled to the distal end of the catheter may be at least partially non-overlapping. The balloons may be inflated with a liquid and/or a gas. The liquid and/or gas used to inflate the balloons may be stored in one or more reservoirs coupled to the proximal end of the catheter.

In an embodiment, the balloons may be configured to be inflated interdependently. The balloons may be coupled to the distal end of the catheter so that, when inflated, the catheter is disposed substantially at the center of the inflated balloons.

In an alternate embodiment, the balloons may be configured to be inflated independently. Independently inflating the balloons may include inflating the balloons with different volumes and/or pressures of fluids and/or gases. Independently inflating the balloons may facilitate the placement of the catheter and a radiation seed residing therein closer to a specified body cavity surface. Independently inflating the balloons may further include inflating each balloon with different liquids and/gases. In an embodiment, one or more of the balloons may be inflated with a fluid and/or a gas that substantially shields surrounding tissue from radiation emitted from a radiation seed.

In embodiments where the distal end of the catheter is coupled to a single balloon, the inner volume of the balloon may be partitioned. Partitioning of the inner volume of the balloon may be achieved by inner support members that couple the outer surface of the catheter to the inner surface of the balloon. The support members, in some embodiments, may substantially dispose the catheter at the center of the inflated balloon. Partitioned inner volumes of a balloon may be sealed from adjacent partitioned inner volumes. Alternatively, partitioned inner volumes of a balloon may be communicably coupled to adjacent partitioned inner volumes.

In an embodiment, a method for delivering a radiation seed to a body cavity may include inserting the distal portion of a brachytherapy apparatus into the body cavity. One or more radiation seeds may be delivered to the distal end of the brachytherapy apparatus. Delivery of the radiation seeds may be accomplished using a seed-loading device. The one or more balloons disposed at the distal end of the brachytherapy apparatus may be inflated with a fluid or gas. Inflating the balloons may result in the catheter and/or radiation seed residing therein to be positioned substantially along a central axis of the inflated balloon. Positioning the catheter and/or radiation seed residing therein along a central axis of the inflated balloon may result in a substantially uniform dose of radiation being delivered to the surrounding tissue.

In an embodiment, the radiation seed delivered to the body cavity through the brachytherapy apparatus may reside in the body cavity for a predetermined amount of time and administer a prescribed dose of radiation to the surrounding tissue.

The apparatus may then be disengaged and removed from the body cavity. Following the brachytherapy procedure, the apparatus may be disposed of. A patient may undergo more than one brachytherapy procedure.

Certain embodiments presented herein may be advantageously suited to performing intrauterine brachytherapy procedures. Certain embodiments presented herein may be advantageously suited to performing brachytherapy procedures on the endometrium of a patient. Certain embodiments presented herein may be advantageously suited to performing brachytherapy procedures to treat at least an early stage endometrial carcinoma.

BRIEF DESCRIPTION OF THE DRAWINGS

Advantages of the present invention will become apparent to those skilled in the art with the benefit of the following detailed description of the embodiments and upon reference to the accompanying drawings, in which:

FIG. 2A depicts cross sectional view of the distal end of a brachytherapy apparatus according to an embodiment;

FIG. 2B depicts a cross sectional view along the longitudinal axis of the distal end of a brachytherapy apparatus according to an embodiment;

FIG. 3 depicts a cross sectional view of the distal end of a brachytherapy apparatus according to an alternate embodiment;

Figure 1:
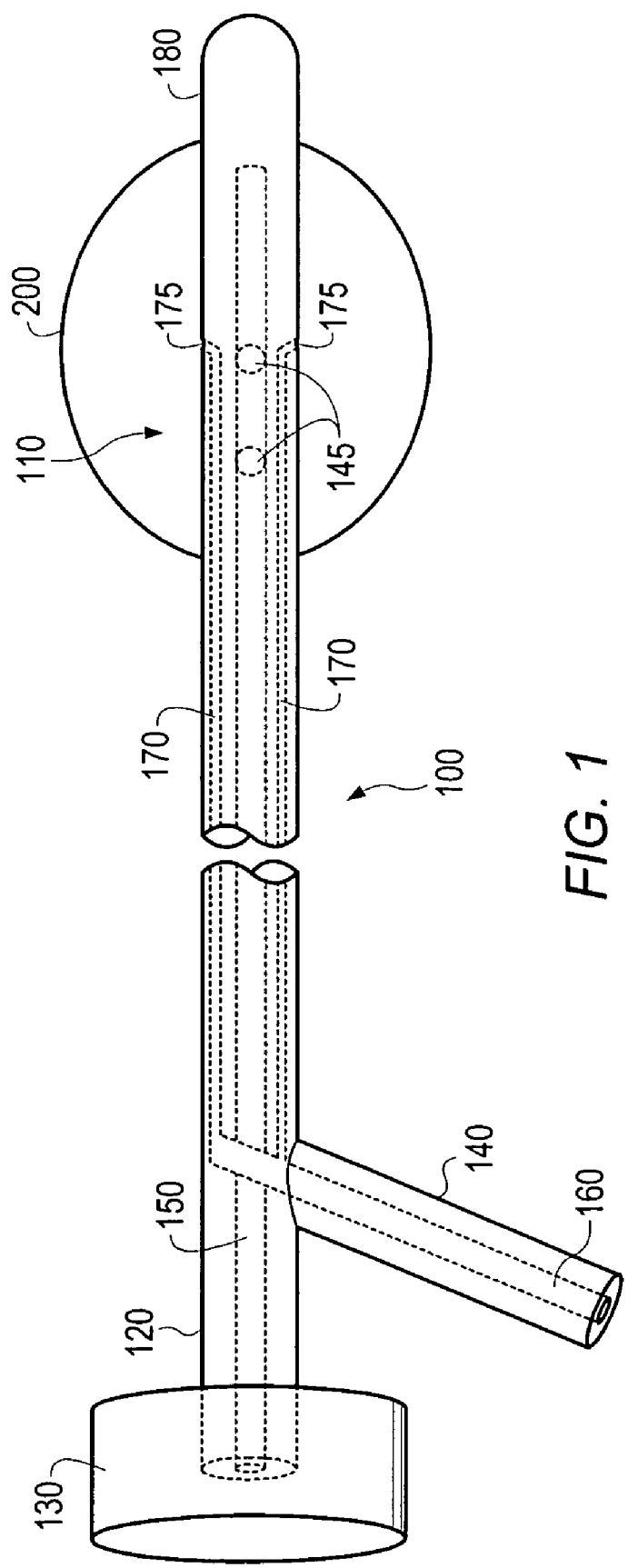
FIG. 1 depicts a longitudinal view of a brachytherapy apparatus according to an embodiment.
Figure 4:
FIG. 4 depicts an image of a pelvic CT scan showing a radiation isodose administered using a single tandem.
Figure 5:
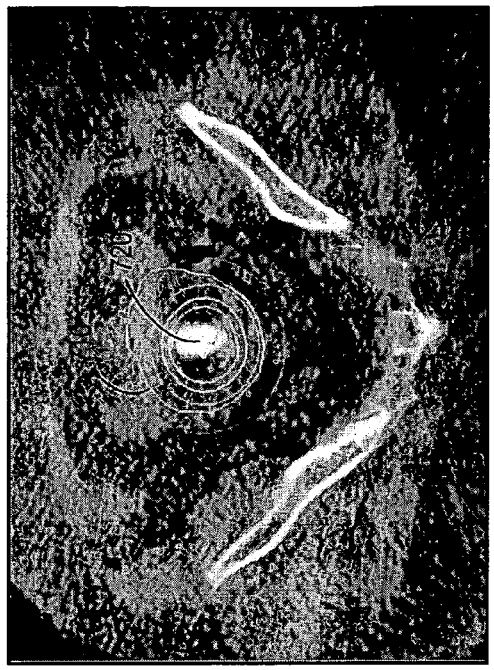
FIG. 5 depicts an image of a pelvic CT scan showing a radiation isodose administered using double tandems.
Figure 6:
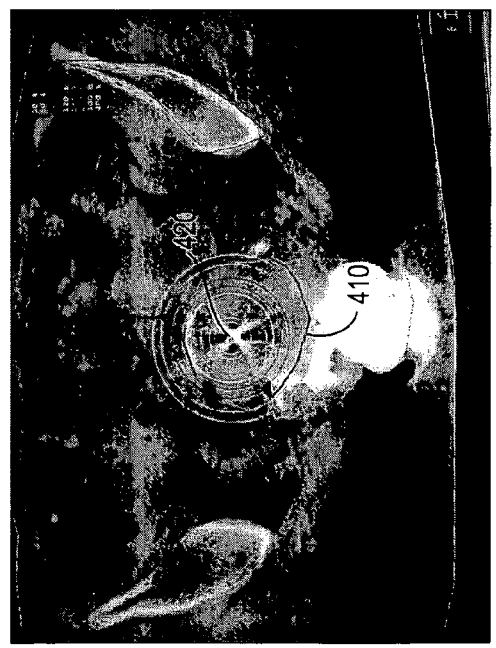
FIG. 6 depicts an image of a pelvic CT scan showing a radiation isodose administered using Heyman capsules.
Figure 7:
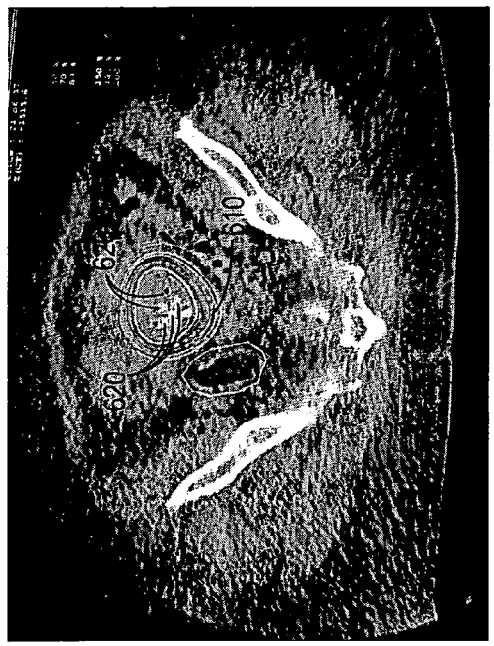
FIG. 7 depicts an image of a pelvic CT scan showing a radiation isodose administered using an inflatable balloon catheter according to an embodiment.

While the invention is susceptible to various modifications and alternative forms, specific embodiments thereof are shown by way of example in the drawings and will herein be described in detail. It should be understood that the drawings and detailed description thereto are not intended to limit the invention to the particular form disclosed, but on the contrary, the intention is to cover all modifications, equivalents and alternatives falling within the spirit and scope of the present invention as defined by the claims appended hereto.

DETAILED DESCRIPTION

Herein is described an apparatus, system and method for administering high dose rate (HDR) brachytherapy on a patient for the treatment of a proliferative disease, such as, for example, a malignancy. The embodiments provided for herein describe an apparatus and system suited to performing brachytherapy in a body cavity of a patient in need thereof. The apparatus is suited to performing, without limitation, brachytherapy on any body cavity of a patient. Certain embodiments provided for herein may be suited to performing intrauterine brachytherapy. Intrauterine brachytherapy may be performed on a patient being treated for an endometrial carcinoma. Certain embodiments provided for herein may be suited to performing brachytherapy in the bladder of a patient. Certain embodiments provided for herein may be suited to performing brachytherapy in the prostate of a patient. Certain embodiments provided for herein may be suited to performing brachytherapy in the esophagus of a patient.

As used herein, the term "brachytherapy" generally refers to a radiation therapy procedure in which a source of radiation is placed close to the surface of the body or within a body cavity. The radiation source may include a radioactive liquid, a gel or a radiation seed. In an embodiment, a radiation source may include a radiation seed. As used herein, the term "radiation seed" may generally be used to denote a solid or substantially solid radioactive particle, plaque, pellet, capsule, needle, wire, or the like, used as a radiation source during a brachytherapy procedure. Apparatuses or systems used to deliver radioactive materials to the anatomic site during a brachytherapy procedure may include, but are not limited to, single or double tandems, Heyman capsules, or partially or fully indwelling catheters. Placement of the catheter at the site of brachytherapy may be temporary, long-term or permanent. In an embodiment, an apparatus used during a brachytherapy procedure to deliver a radiation seed to a substantially internal site of the body may include a catheter.

As used herein, the term "catheter" generally refers to an elongated tubular medical device that may be inserted into natural or surgically created body cavities, canals, vessels, or passageways. A catheter generally includes one or more lumens that extend along the length of the body of the catheter. A lumen may, in some embodiments, permit the flow of a fluid or a gas from one end of the catheter, though the lumen, and out the distal end of the catheter. As used herein, the term "lumen" generally refers to a hollowing or a space of a measurable volume that extends into an otherwise substantially solid object or body organ. In some embodiments, a lumen may refer to the bore of a tube, such as, for example, the hollow of a needle or a catheter.

As used herein, the term "body cavity" generally refers to any inner or open space of a tissue or of a body organ. In an embodiment, a body cavity may refer to a surgically created space within a body or tissue, such as would occur following the surgical removal of at least a portion of diseased and/or healthy tissue. In some embodiments, a body cavity may refer to the interstitial space between two substantially adjacent organs or tissues. In other embodiments, a body cavity may refer to one or more of the peritoneal, pleural, or pericardial cavities of a patient. In yet further embodiments, a body cavity may refer to a space, or a lumen, within a body organ. Non-limiting examples of body organs with cavities or lumens may include blood or lymphatic vessels, cardiac atria and ventricles, pharynx, esophagus, stomach, intestines, lung, bronchi, urinary bladder, prostate, ducts of the genitourinary system, uterus, rectum, nasopharynx, gall bladder, bile duct, trachea, oral cavity, auditory canals, or any other organ or body part with a discernible cavity, such as would be readily recognized by an ordinary practitioner of the art.

In some embodiments, a brachytherapy apparatus may include a catheter body 100 with a distal end 110 and proximal end 120, as shown in FIG. 1. At least a portion of catheter body 100 may be made of a physiologically inert, flexible material. Catheter body 100 may be made of materials including, but not limited to, latex, silicone, plastic, polymer, metal, and/or mixtures thereof. Catheter body 100 may be at least partially made of a material that substantially resists puncture and/or breakage. Catheter body 100 may be configured such that during insertion in a body, a lumen of the catheter may not substantially collapse. In an embodiment, at least a portion of catheter body 100 may be rigid. Catheter body 100 may be adapted to substantially withstand temperature, pressure, and/or pH changes in a body. Catheter body 100, or portions thereof, may be at least partially made of one or more radioopaque materials. Catheter body 100 may include radioopaque markers that facilitate verification of the correct placement of at least a portion of the catheter body using radiological visualization. Radiological means that may be used to determine the location and placement of at least a portion of catheter body 100 in the body cavity are well known in the art and may include, but are not limited to, X-ray, contrast-enhanced X-ray, computer assisted tomography (CT scan), magnetic resonance imaging (MRI) or ultrasound. Correct placement of catheter body 100 in the body cavity may substantially ensure that an optimal radiation isodose is administered to the surrounding tissue.

A catheter body may have a shape similar to catheters known to one skilled in the art. In some embodiments, catheter body 100 may have a substantially circular, substantially oval, substantially rectangular, or irregular cross sectional shape. In an embodiment, the cross-sectional area of catheter body 100 may change along the longitudinal axis of the body. Catheter body 100 may be substantially tubular. Catheter body 100 may be a single, double, triple, or a multiple lumen catheter. In one embodiment, catheter body 100 may include 2 lumens. In an embodiment, catheter body 100 may include 3-5 lumens The length of catheter body 100 may be sufficient so that at least a portion of the catheter body resides at a desired site within a body cavity. In an embodiment, catheter body 100 may be approximately 5-60 cm long. In an embodiment, catheter body 100 may be approximately 20-60 cm long. In an embodiment, catheter body 100 may be approximately 10-50 cm long. In an embodiment, catheter body 100 may be approximately 25-35 cm long. In an embodiment, catheter body 100 may be approximately 30 cm long. Distal end 110 may be positionable in a body cavity of a patient. Proximal end 120 may remain outside the body cavity of a patient. Proximal end 120 may be positioned outside the body of the patient so as to be accessible by medical devices used during the procedure and/or by personnel performing the procedure. Proximal end 120 may include an adaptor 130, such as that which is shown in FIG. 1. Adaptor 130 may be configured to be couplable to one or more medical devices. In an embodiment, adaptor 130 may be configured to be couplable to a remote afterloader. Adaptor 130 may be configured to allow the insertion of one or more radiation seeds into a lumen of catheter body 100.

In some embodiments, catheter body 100 may include one or more lumens. The lumens may extend substantially along the length of the catheter body. The lumens may be disposed within the catheter body substantially adjacent to one another. Some of the lumens may, in some embodiments, be continuous with each other. Some of the lumens may not be continuous with each other. The cross sectional shape of one or more of the lumens may be similar to lumens familiar to practitioners of the art. Cross sectional shapes of the lumens may be substantially circular, substantially oval, substantially rectangular, or may be irregular. The cross sectional area of one or more of the lumens may vary at different positions along the length of catheter body 100.

Returning to FIG. 1, in an embodiment at least one of the lumens may be adapted to receive one or more radiation seeds 145. Receiving a radiation seed may include providing the radiation seed to radiation seed lumen 150 from a medical device coupled to adapter 130. Such a device may include, for example, a remote afterloader.

In an embodiment, radiation seed lumen 150 may be continuous along the outer surface of proximal end 120. Radiation seed lumen 150 may extend substantially along the length of catheter body 100 to distal end 110. In an embodiment, radiation seed lumen 150 may be continuous with outer surface of distal end 110. In another embodiment, radiation seed lumen 150 may be sealed from the outer surface of distal end 110. For illustrative purposes only, FIG. 1 depicts an embodiment of a brachytherapy apparatus with only one radiation seed lumen. It will be readily appreciated by an ordinary practitioner of the art, however, that a catheter body may be configured with a plurality of radiation seed lumens. Different radiation seed lumens may, in some embodiments, be of different length. Different radiation seed lumens may, in some embodiments, be of different diameter. Different radiation seed lumens may, in some embodiments, be adapted to hold different numbers or types of radiation seeds.

In some embodiments, radiation seed 145 may be disposed in radiation seed lumen 150 at the time the catheter body is manufactured. In such embodiments, adapter 130 may or may not be included. In such embodiments, radiation seed lumen 150 may or may not be continuous with the outer surface of proximal end 120. Manufacturing radiation seeds into catheter body 100 may, in some embodiments, obviate the need for radiation seed lumen 150. Manufacturing radiation seeds into catheter body 100 may include substantially embedding the radiation seed in at least a portion of the catheter body. In another embodiment, manufacturing radiation seeds into catheter body may include chemically bonding a radioactive material into the material used to make the catheter body.

In an embodiment, the radiation seeds may be disposed in a lumen that lies substantially at the center of catheter body 100, as shown in FIG. 2A and FIG. 2B. In an embodiment, more than one radiation seed may be disposed in a radiation seed lumen. The number and configuration of radiation seeds 145 used in a brachytherapy procedure may depend on several factors including but not limited to, the type of tumor, the location of the tumors, the size of the tumor, the size and shape of the body cavity, and the general health of the patient. In an embodiment, an HDR brachytherapy procedure may include delivering >0.5 Ci of radiation to the organ. In an embodiment, an HDR brachytherapy procedure may include delivering >5.0 Ci of radiation to the organ. In an embodiment, an HDR brachytherapy procedure may include delivering >10 Ci of radiation to the organ. The types of radionuclides generally suitable for use in brachytherapy procedures are known to ordinary practitioners of the art. In some embodiments, preferred radionuclides for HDR brachytherapy applications may include those radionuclides that emit gamma radiation. For purposes of illustration only, some non-limiting examples of radionuclides and the form that they may take that are suitable for use in some of the embodiments described herein are summarized in Table I.

Returning to FIG. 1, in some embodiments, proximal end 120 of catheter body 100 may be coupled to a port 140. Port 140 may be adapted to allow an operator to introduce a fluid or a gas into a lumen of catheter 100. Port 140 may include one or more filling lumens 160 that are continuous with one or more lumens of catheter body 100. In an embodiment, filling lumen 160 may be continuous with one or more conducting lumens 170 in catheter body 100. In an embodiment, conducting lumens 170 may extend substantially along the length of catheter body 100 to distal end 110. Conducting lumens 170 may be coupled to one or more outlets 175 on the outer surface 180 of distal end 110 as shown in FIGS. 2A and 2B. While FIG. 2B depicts an embodiment that includes two outlets 175 that are located approximately equidistantly from the tip of distal end 110, it will be readily appreciated by a practitioner of ordinary skill in the art that alternative configurations of outlets 175 may be possible. Additionally, although only a single outlet 175 is depicted along a longitudinal axis of catheter body 100 in FIG. 2B, it will be readily appreciated by a practitioner of ordinary skill in the art that a plurality of outlets 175 may be located along a longitudinal axis of a catheter body. Outlets 175 may include an opening to conducting lumen 170 that is at least partially continuous with outer surface 180 of distal end 110.

TABLE I

| Radionuclide | Typical form | Typical application |
|---|---|---|
| 60-Co | pellets | HDR remote after loading |
| 125-I | particles | Permanent or temporary volume implants |
| 137-Cs | needles, pellets, tubes | LDR remote afterloading |
| 192-Ir | hairpin, wires, HDR sources | Interstitial implants, HDR and LDR remote afterloading |
| 198-Au | seeds | Permanent volume implants |
| 226-Ra | needles | No longer in common use |

In an embodiment, port 140 may be adapted to be coupled to one or more fluid or gas reservoirs. Fluid or gas reservoirs suitable for coupling to port 140 are known in the art and may include, but are not limited to, a syringe, or an ampoule adapted for coupling to port 140. In an embodiment, a fluid or gas reservoir may be adapted to be independently coupled to only a subset of filling lumens 160 and/or conducting lumens 170. A fluid or gas reservoir may be adapted to hold a fluid or a gas that may be introduced into catheter body 100 through port 140. The fluid and/or gas, in an embodiment, may include a contrasting or radio-opaque material that may be visualized radiologically. The fluid and/or gas may include a material that at least partially absorbs and/or deflects radioactive emissions. Absorbing and/or deflecting at least a portion of radiation emitted from a radiation seed may shield surrounding tissue from some of the deleterious effects of radiation exposure. The fluid and/or gas may be substantially physiologically inert and non-toxic. At least a portion of a fluid may be a saline solution. Introducing a fluid or gas into filling lumen 160 may cause the fluid or gas to flow from filling lumen 160, through the one or more conducting lumens 170 and out the one or more outlets 175 at distal end 110. In other words, the filling lumen 160, conducting lumens 170 and outlet 175 may be configured to allow the continuous flow of a fluid or gas from a fluid or gas reservoir coupled to port 140 to outer surface 180 of distal end 110.

In some embodiments, distal end 110 of catheter body 100 may be coupled to an inflatable balloon 200. Inflatable balloon 200 may be made of a substantially distensible, physiologically inert, non-toxic material. Materials that are distensible and that may be used in embodiments presented herein are known in the art and may include, but are not limited to, latex, rubber, silicon rubber, reinforced rubber, polymeric films, or the like. Balloons for medical catheters and methods of making same are well known to practitioners in the art and are described in U.S. Pat. No. 6,787,095 entitled "Process for manufacturing polybutylene terephthalate (PBT) catheter balloons", U.S. Pat. No. 6,765,059 entitled "Polymer material", U.S. Pat. No. 6,761,786 entitled "Process of making a balloon for an intraluminal catheter", U.S. Pat. No. 6,730,377 entitled "Balloons made from liquid crystal polymer blends", U.S. Pat. No. 6,712,833 entitled "Method of making a catheter balloon", U.S. Pat. No. 6,712,832 entitled "Low-pressure medical balloons and method of making same", all of which are incorporated by reference as though fully set forth herein. In an embodiment, balloon 200 may be made of a substantially rupture resistant material. A non-limiting example of a suitable rupture resistant material that may be used includes nanocomposite films.

Inflatable balloon 200 may be configured to be inflated by a fluid or gas that flows from outlets 175. Turning to FIG. 2A, balloon 200 may have an outer wall 210 that is distensible when balloon 200 is inflated with a fluid or a gas flowing from outlets 175. In an embodiment, the radial distance from outer wall 210 to a radiation seed 145 disposed in radiation seed lumen 150 may be substantially uniform along the circumference of outer wall 210. In an embodiment, outer wall 210 may be configured so that the radial distance from outer wall 210 to a radiation seed 145 disposed in radiation seed lumen 150 may be variable along the circumference of outer wall 210. In some embodiments, the general shape of balloon 200, when inflated, may be substantially spherical. In some embodiments, the general shape of balloon 200, when inflated, may be substantially ovoid. In some embodiments, the general shape of balloon 200, when inflated, may in part be determined by the target body cavity. In some embodiments, the general shape of balloon 200, when inflated, may be configured to substantially conform to the anatomical volume of the body cavity. In some embodiments, the general shape of balloon 200, when inflated, may be configured to substantially conform to the anatomical volume of the body cavity when distended. In some embodiments, the general shape of balloon 200, when inflated, may be configured to substantially conform to the anatomical volume of the uterus. Configuring the three dimensional shape of the inflated balloon to substantially complement the three-dimensional shape of the body cavity may help to ensure that a substantially uniform radiation isodose is administered to the target organ. As used herein, the term "radiation isodose", or more simply "isodose", generally refers to points in three-dimensional space that receive substantially equal doses of radiation from a radioactive source.

In an embodiment, balloon 200 may be comprised of a plurality of balloons. In an embodiment, two or more balloons 200 may be independently coupled to distal end 110. The two or more balloons coupled to distal end 110 may be at least partially non-overlapping. In the context of the present embodiments, the term "non-overlapping balloons" generally refers to substantially adjacent balloons whose inner volumes 220 are mutually exclusive. In an embodiment, two or more at least partially non-overlapping balloons may be separated by balloon wall 230. In an embodiment, each inner volume 220 may be inflated with fluid or gas from a distinct outlet 175. In an embodiment, each inner volume 220 may be inflated with fluid or gas from a plurality of distinct outlets 175.

In an embodiment, the two or more at least partially non-overlapping balloons may be configured so that, when inflated, at least a potion of distal end 110, radiation seed lumen 150, and any radiation seeds 145 residing therein, may be disposed on an axis that passes through substantially the center of the inflated balloons, such as, for example, as is depicted in FIGS. 2A and 2B. In an embodiment, disposition of the these elements at an axis that passes through substantially the center of the inflated balloons may be at least in part stabilized by balloon walls 230. In an embodiment, disposing the catheter on an axis that passes through substantially the center of the inflated balloons may administer a substantially uniform radiation isodose to the surrounding tissue. Such configurations may be advantageous for certain applications such as, for example, when administering intrauterine brachytherapy. Such configurations may be advantageous for certain applications such as, for example, when administering intracavitary brachytherapy to treat endometrial carcinoma.

In some embodiments, rather than coupling two or more at least partially non-overlapping balloons to distal end 110, only a single balloon 200 may be used. In such embodiments, outer wall 210 may be coupled to inner surface 180 by one or more radial coupling members 240. Radial coupling members may, in an embodiment, be made of the same material as outer wall 210 of balloon 200. Radial coupling members may, in an embodiment, be made of different materials than outer wall 210 of balloon 200. In some embodiments, radial coupling members may dispose the catheter, and the radiation seeds 145 residing therein on an axis that substantially passes through substantially the center of the inflated balloons.

In an embodiment, distension of balloon 200 may vary according to the volume of fluid that flows from outlet 175. The volume that balloon 200 may be distended during a brachytherapy procedure may be determined by the physician performing the procedure. Determination of the volume by which balloon 200 should be distended may vary according to the situation and is within the skill level of an ordinary practitioner of the art.

In an alternate embodiment, each inner volume 220 may be adapted to be inflated independently of other inner volumes 220. Independently inflating an inner volume 220 may allow an operator to inflate each inner volume 220 with different volumes of a fluid and/or a gas. Inflating each inner volume 220 with different volumes of a fluid and/or a gas may allow an operator to intentionally position a radiation seed 145 closer to a desired surface of a body cavity. Independently inflating an inner volume 220 may also allow an operator to inflate one or more of the balloons with a fluid and/or a gas that includes a material that at least partially absorbs and/or deflects radioactive emissions, thus shielding at least a portion of the tissue or body organ surrounding the catheter and the radiation seed from the radiation source. Positioning a radiation seed closer to a particular body cavity surface and/or partially shielding surrounding tissue from radioactive emission may be advantageously suited to intracavitary brachytherapy applications where it is desirable to provide a more directed dose radiation than is typically applied during an intrauterine brachytherapy procedure. Directing a radiation dose to a desired surface of a body cavity or surface may enable an operator to treat an unhealthy portion of tissue, such as for example, a localized tumor, with an appropriate radiation dose, while substantially or partially reducing the dose of radiation applied to surrounding tissue, or shielding surrounding tissue from the deleterious effects of radiation exposure.

FIG. 3 depicts an embodiment in which inner volumes 220 may be inflated independently of each other. For purposes of illustration only, the embodiment represented in FIG. 3 depicts four independently inflatable balloons. It will be readily appreciated by an ordinary practitioner of the art however, that this depiction is non-limiting, and that additional embodiments may make use of different numbers of balloons. To facilitate understanding of such an embodiment, different inner volumes 220 have been arbitrarily assigned the identifiers A, B, C and C', as shown in FIG. 3.

In an embodiment, an operator may wish to direct a dose of radiation from radiation seed 145 preferentially toward a particular surface of a body organ. For example, an operator may wish to preferentially irradiate tumor 340, located in lumen 350 of body organ 360, while minimizing the dose of radiation administered to healthy tissue lining lumen 350. In an embodiment, an operator may provide inner volume A with a higher fluid and/or gas pressure than that which is provided to inner volume B. Inner volumes C and C' may be provided with substantially similar fluid and/or gas pressures. Inflating inner volume A with a greater fluid and/or gas pressure than inner volume B may allow outer surface 180 of distal end 110 to be positioned closer to tumor 340 than would be achieved if the pressure of inner volumes A, B, C and C' were substantially similar.

In an embodiment, directing a radiation dose to a particular lumen surface may further include inflating inner volumes A and/or C and/or C' with a fluid and/or a gas that includes a material that at least partially absorbs and/or deflects radioactive emissions. Inflating inner volumes A and/or C and/or C' with such a fluid may be performed independently of inflating inner volumes A and B with different fluid and or gas pressures.

In an embodiment, a procedure to place one or more radiation seeds in a body cavity to perform a brachytherapy procedure may include inserting distal end 110 of catheter body 100 into the body cavity. The depth to which distal end 110 should be inserted into the body cavity may vary according to each situation. Determination of the appropriate depth to which distal end 110 should be inserted into the body cavity is within the skill level of an ordinary practitioner of the art. Inserting distal end 110 to the correct location in the body cavity may include using radiological procedures.

After distal end 110 is properly positioned within the body cavity, balloon 200 may be inflated with a fluid or gas from a reservoir coupled to port 140. The reservoir may be coupled to port 140 before distal end 110 is inserted into the body cavity. Alternatively, the reservoir may be coupled to port 140 after distal end 110 is appropriately positioned. Fluid or gas may be caused to flow from the reservoir into filling lumen 160, conducting lumens 170, and through outlets 175 to fill inner volume 220. In one embodiment, inflating the balloon may cause the walls of the body cavity to substantially conform to the three dimensional shape of the inflated balloon. In an embodiment, the balloon may be configured such that, when inflated, the balloon substantially conforms to the three-dimensional shape of the body cavity. Deflation of the balloon may, in some embodiments, be substantially prevented by engaging one or more stop valves that may be included on port 140, along filling lumen 160 or along conducting lumens 170. Disengaging the stop valves may allow deflation of balloon 200 at termination of the procedure to facilitate withdrawal of catheter body 100 from the body cavity.

One or more radiation seeds may be placed into radiation seed lumen 150. Typically, the radiation seeds will be placed in a location along radiation seed lumen 150 toward a portion of distal end 110 that is positioned within the body cavity. The number, type and location of radiation seeds to be disposed within radiation seed lumen 150 may vary according to each situation. Determination of the appropriate number, type and location of radiation seeds to be placed within radiation seed lumen 150 is within the skill level of an ordinary practitioner of the art. The radiation seeds may, in some embodiments, be placed manually. In other embodiments, radiation seeds may be placed using a remote afterloader. Placement of radiation seeds using a remote afterloader may be partially or fully automated. The radiation seeds may dwell in the positioned catheter body 100 for a period of time that is adequate to irradiate the body cavity with a dose of radiation prescribed by a physician. The amount and configuration of a radiation isodose administered to the body cavity may be determined using known techniques, which may include analytical systems such as, for example, HDR PLATO Brachytherapy Planning System (v14.2.3) available from Nucletron Corp.

In an embodiment, radiation seeds may be disposed in radiation seed catheter prior to insertion of the catheter in the body cavity. In an embodiment, radiation seeds may be disposed in the material of catheter body 100 at the time the catheter body is manufactured.

Following administration of the prescribed dose or radiation to the body cavity, the one or more balloons may be deflated, and the catheter withdrawn from the body. Typically, the brachytherapy apparatus described herein will be disposable. The brachytherapy apparatus will be disposed of following its withdrawal from the body cavity.

The invention and its use will now be illustrated by examples, which are to be regarded as illustrative and not delimitative of the invention.

EXAMPLE 1

Dosimetric analyses were performed on patients undergoing intrauterine brachytherapy using Fletcher-type single tandem or double tandems with ovoids, disposable afterloading type Heyman capsules (in the case shown here, eight capsules were used), or a brachytherapy apparatus according to an embodiment (wherein the balloon was inflated with an approximate volume of 40 cc saline), to assess the dose homogeneity and conformality indices for the treatment of endometrial cancer. Treatment planning and dosimetric analyses were done with HDR PLATO Brachytherapy (v14.2.3) software from Nucletron Corp.

The results obtained from different brachytherapy procedures are depicted in pelvic CT scans shown in FIGS. 4-7. The sample isodose lines are indicated as elements 410, 510, 610, and 710 in FIG. 4, FIG. 5, FIG. 6, and FIG. 7, respectively. Optimal planned isodose lines are shown as light concentric circles. The location of the radioactive source generated by the different apparatuses are indicated as elements 420, 520, 620, and 720 in FIG. 4, FIG. 5, FIG. 6, and FIG. 7, respectively.

The average dose gradient within the target (uterine wall) is highest with the tandem methods, and closely followed by Heyman capsules. The embodied method showed the least dose gradient across the uterine wall. The corresponding average homogeneity indices are 3.81, 3.83, 2.97, 2.50 for single tandem, double tandem, Heyman capsules, and the embodied method respectively. With respect to dose homogeneity indices, lower values are considered to be best. With proper optimization, the 3-D dose clouds of Heyman capsules and the embodied method conform to the shape of the uterus better than single or double-tandem methods, especially in the anterior-posterior (AP) direction as suggested by the conformality indices, wherein a conformatlity index of 1 is considered to be optimal. The results obtained using these various intrauterine brachytherapy procedures are summarized in Table II.

TABLE II

| Indices | Single Tandem (with ovoids) | Double Tandem (with ovoids) | Heyman Capsules | Inflatable Balloon |
|---|---|---|---|---|
| Homogeneity* | 3.81 | 3.83 | 2.97 | 2.50 |
| Conformality** | 2.33 | 1.32 | 1.16 | 1.20 |

*Homogeneity index = (inner uterine wall dose)/(outer surface dose)
**Conformality Index = (target volume)/(treatment volume)

The currently embodied system appears to have the best overall dosimetric advantages for the treatment of uterine wall. The corresponding average homogeneity and conformality indices for single tandem, double tandem, Heyman capsules, and inflatable balloon were 3.81/2.33, 3.83/1.32, 2.97/1.16, and 2.50/1.20 respectively. Furthermore, the potential ease of use, shorter time of treatment procedure, and better patient comfort using the embodied system suggest that this system may be at least somewhat advantageous over other intrauterine brachytherapy systems.

In this patent, certain U.S. patents, U.S. patent applications, and other materials (e.g., journal articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes may be made in the elements described herein without departing from the spirit and scope of the invention as described in the following claims. In addition, it is to be understood that features described herein independently may, in certain embodiments, be combined.

What is claimed is:

1. A body cavity brachytherapy apparatus comprising:
   a catheter body having a distal end and a proximal end, wherein the distal end is positionable substantially adjacent to a body cavity surface of a subject;
   two or more lumens extending at least partially along the length of the catheter body, at least one of the lumens being a first lumen, wherein the first lumen is configured to accept a radiation seed; and
   an inflatable balloon coupled to the distal end of the catheter body, said balloon comprising an outer wall defining a first volume, and a plurality of inner walls extending longitudinally along at least a portion of the distal end of the catheter body and coupling the outer wall to the distal end of the catheter body and partitioning the first volume of the balloon into a plurality of inflatable inner volumes, wherein the inner walls are configured such that, when the inner volumes are equally inflated, at least a portion of the distal end of the catheter body remains positioned at substantially the center of the first volume, wherein the inner volumes are adapted to be inflated with a liquid or a gas delivered though a lumen other than the first lumen; and wherein at least a portion of the inflatable balloon is positioned such that radiation from a radiation seed disposed in the first lumen passes through the balloon to the body cavity surface during use.

2. The apparatus of claim 1, wherein the catheter body is between about 5 cm to about 60 cm long.

3. The apparatus of claim 1, further comprising a reservoir coupled to the proximal end of the catheter body, wherein the reservoir is configured to hold the fluid or gas that inflates the balloon.

4. The apparatus of claim 3, wherein the reservoir is coupled to the balloon though one or more of the lumens, and wherein coupling the reservoir to the lumens allows the fluid or gas to flow between the reservoir and the balloon.

5. The apparatus of claim 1, further comprising an adapter coupled to the proximal end of the catheter body, wherein the adapter is configured to provide a radiation seed to a lumen.

6. The apparatus of claim 1, wherein the apparatus is adapted to administer endometrial brachytherapy to a subject.

7. The apparatus of claim 1, wherein each of the inner volumes is independently inflatable.

8. The apparatus of claim 1, wherein the inflatable balloon comprises at least 3 inner walls.

9. The apparatus of claim 1, wherein the inflatable balloon comprises at least 3 independently inflatable inner volumes.

10. The apparatus of claim 1, wherein the inflatable balloon comprises at least 4 inner walls.

11. The apparatus of claim 1, wherein the inflatable balloon comprises at least 4 independently inflatable inner volumes.

12. The apparatus of claim 1, wherein the first lumen is configured to accept a plurality of radiation seeds.

13. The apparatus of claim 1, further comprising one or more additional lumens configured to accept one or more radiation seeds.

14. The apparatus of claim 1, further comprising a plurality of conducting lumens, each conducting lumen coupled to a separate inner volume, wherein each conducting lumen is configured to independently conduct fluid to each inner volume.

15. The apparatus of claim 1, wherein the inflatable balloon substantially surrounds a radiation seed disposed in the distal end of the catheter body.

16. A body cavity brachytherapy system comprising: a brachytherapy apparatus, the brachytherapy apparatus comprising:
  a catheter body having a distal end and a proximal end, wherein the distal end is positionable substantially adjacent to a body cavity surface of a subject;
  two or more lumens extending at least partially along the length of the catheter body, at least one of the lumens being a first lumen, wherein said first lumen is configured to accept a radiation seed; and
  an inflatable balloon coupled to the distal end of the catheter body, said balloon comprising an outer wall defining a first volume, and a plurality of inner walls extending longitudinally along at least a portion of the distal end of the catheter body and coupling the outer wall to the distal end of the catheter body and partitioning the first volume of the balloon into a plurality of inflatable inner volumes, wherein the inner walls are configured such that, when the inner volumes are equally inflated, at least a portion of the distal end of the catheter body remains positioned at substantially the center of the first volume, wherein the inner volumes are adapted to be inflated with a liquid or a gas delivered though a lumen other than the first lumen, and wherein at least a portion of the inflatable balloon is positioned such that radiation from a radiation seed disposed in the first lumen passes though the balloon to the body cavity surface during use; and
  one or more radiation seeds disposed in the first lumen.

17. The system of claim 16, wherein one or more of the inner volumes is inflatable with a liquid or a gas comprising a material that at least partially absorbs or at least partially deflects radioactive emissions.

18. The system of claim 16, wherein the balloon is adapted to be inflated with a liquid or a gas that flows from at least one of the catheter lumens.

19. The system of claim 16, wherein the catheter body is from about 5 cm to about 60 cm long.

20. The system of claim 16, wherein one or more of the radiation seeds are disposed in the first lumen such that, when inserted into a body cavity of a subject, the one or more radiation seeds irradiate at least a portion of the body cavity.

21. The system of claim 16, wherein the radiation seeds comprise iridium.

22. The system of claim 16, wherein the radiation seeds comprise between about 0.5 Ci to about 20 Ci of a gamma-emitting radioisotope.

23. The apparatus of claim 16, wherein each of the inner volumes is independently inflatable.

24. The apparatus of claim 16, wherein at least one of the inner volumes is inflated unequally from the remaining inner volumes during use such that the one or more radiation seeds disposed in the first lumen are positionable at a desired location relative to the body cavity surface undergoing brachytherapy.

25. The apparatus of claim 16, wherein a plurality of radiation seeds are disposed in the first lumen.

26. The apparatus of claim 16, further comprising one or more additional lumens, each additional lumen having one or more radiation seeds disposed therein.

27. The apparatus of claim 16, further comprising a plurality of conducting lumens, each conducting lumen coupled to a separate inner volume, wherein each conducting lumen is configured to independently conduct fluid to each inner volume.

28. The apparatus of claim 16, wherein the inflatable balloon substantially surrounds a radiation seed disposed in the distal end of the catheter body.

* * * * *

UNITED STATES PATENT AND TRADEMARK OFFICE
CERTIFICATE OF CORRECTION

PATENT NO. : 7,534,202 B2 Page 1 of 1
APPLICATION NO. : 11/243474
DATED : May 19, 2009
INVENTOR(S) : Tony Y. Eng It is certified that error appears in the above-identified patent and that said Letters Patent is hereby corrected as shown below:

In the Claims:

Claim 4, col. 15, line 6, please delete "though" and substitute therefor -- through --.

Signed and Sealed this

Fourteenth Day of July, 2009

JOHN DOLL
*Acting Director of the United States Patent and Trademark Office*